US008776402B2

(12) United States Patent
Cromer, Jr.

(10) Patent No.: US 8,776,402 B2
(45) Date of Patent: Jul. 15, 2014

(54) ANKLE INVERSION AND EVERSION PREVENTION SHOE

(71) Applicant: Ronnie E. Cromer, Jr., Farmington Hills, MI (US)

(72) Inventor: Ronnie E. Cromer, Jr., Farmington Hills, MI (US)

(73) Assignee: RTC3 LLC, Southfield, MI (US)

( * ) Notice: Subject to any disclaimer, the term of this patent is extended or adjusted under 35 U.S.C. 154(b) by 0 days.

(21) Appl. No.: 13/888,127

(22) Filed: May 6, 2013

(65) Prior Publication Data

US 2013/0245525 A1 Sep. 19, 2013

Related U.S. Application Data

(60) Provisional application No. 61/687,966, filed on May 5, 2012, provisional application No. 61/688,408, filed on May 14, 2012.

(51) Int. Cl.
*A43B 5/00* (2006.01)

(52) U.S. Cl.
USPC .................................. 36/112; 36/132; 36/136

(58) Field of Classification Search
CPC ............ A43B 5/00; A43B 5/001; A43B 7/14; A43B 7/20; A43B 7/24
USPC ................ 36/88, 89, 112, 114, 132, 136, 116
See application file for complete search history.

(56) References Cited

U.S. PATENT DOCUMENTS

| 1,870,751 | A | * | 8/1932 | Reach | 36/127 |
| 4,314,413 | A | * | 2/1982 | Dassler | 36/129 |
| 4,366,634 | A | | 1/1983 | Giese et al. | |
| 4,566,209 | A | * | 1/1986 | Johnson | 36/116 |
| 4,748,753 | A | * | 6/1988 | Ju | 36/127 |
| 4,790,083 | A | * | 12/1988 | Dufour | 36/127 |
| 5,109,613 | A | | 5/1992 | Van Dyke | |
| 5,875,569 | A | * | 3/1999 | Dupree | 36/103 |
| 6,474,006 | B1 | * | 11/2002 | Cummings et al. | 36/142 |
| 7,849,611 | B2 | * | 12/2010 | Dean | 36/89 |
| D634,918 | S | * | 3/2011 | Katz et al. | D2/902 |
| D635,748 | S | * | 4/2011 | Katz et al. | D2/902 |
| 7,918,811 | B2 | | 4/2011 | Lussier et al. | |
| 8,327,560 | B2 | * | 12/2012 | Berend | 36/92 |
| 2009/0260259 | A1 | * | 10/2009 | Berend | 36/88 |
| 2011/0056097 | A1 | | 3/2011 | Ellis, III | |
| 2012/0102787 | A1 | * | 5/2012 | Haskell | 36/136 |

* cited by examiner

*Primary Examiner* — Marie Bays
(74) *Attorney, Agent, or Firm* — Brooks Kushman P.C.

(57) ABSTRACT

An ankle inversion and eversion prevention athletic shoe has an upper foot support portion and a shoe bottom. The ankle inversion and eversion athletic shoe device is designed for preventing an athlete from spraining or turning or rolling an ankle during normal athletic competition or play or activities. The shoe includes a brace. The brace is located either behind the ankle on a heel of the shoe or on a side of said shoe in the general vicinity of the ankle. The brace includes an elongated arm and a floor contact surface designed to limit or control sliding of the foot to enable wearer time to regain composure, footing and balance. The brace provides the wearer time to regain his or her balance onto the shoe bottom, thus significantly limiting or precluding the typical and usually unavoidable ankle injury.

17 Claims, 12 Drawing Sheets

FIGURE 1A
SIDE VIEW

FIGURE 1B
ASSEMBLY VIEW

FIGURE 2
TOP VIEW

FIGURE 3
TOP VIEW

FIGURE 4
TOP VIEW

FIGURE 5
SIDE VIEW

FIGURE 6
TOP VIEW

FIGURE 7
TOP VIEW

ANKLE INVERSION AND EVERSION PREVENTION SHOE

This application is related to and claims priority to U.S. Provisional Application No. 61/687,966, entitled "Ankle Inversion Prevention Shoe," filed on May 5, 2012; and U.S. Provisional Application No. 61/688,408, entitled "Ankle Inversion Prevention Shoe," filed on May 14, 2012.

FIELD OF USE

The present invention relates to an ankle inversion or eversion prevention athletic shoe or device which allows for the placement of a fixed, reinforced brace support, which extends from the outer, or optional inner surface of the athletic shoe, reinforced, lightweight material that is designed to prevent ankle sprains and rolls caused by inversion or eversion of the ankle when the foot is inadvertently misplaced against an object or when a disproportionate amount of weight is placed on the ankle while the athlete is engaged in rigorous sports activities (including but not limited to basketball, jogging, running and on-court activities).

BACKGROUND OF THE INVENTION

Sprained ankles are the most frequent type of musculoskeletal injury seen by primary-care providers. More than 23,000 people each day in the United States require medical care for ankle sprains.[1] Several muscles control motion at the ankle with each having a tendon connecting the ankle to one or more of the bones of the foot.

[1] http://www.emedicinehealth.com/ankle sprain/article em.htm

Tendons can be stretched or torn when the joint is subjected to greater than normal stress. Chronic inflammation of a stretched or torn tendon is called tendinitis. Tendons also can be pulled off the bone, called an avulsion injury. Ligaments provide connection between bones. Sprains are injuries to the ligaments.

The ligaments are structures that control excessive movement of the joint. When an ankle sprain occurs, the ligament is overstretched, and is either partially or completely torn. This most commonly happens when the foot is turned inward or inverted. This kind of injury can happen by awkwardly planting the foot when running or stepping up or down on an unstable surface.

A common example is a basketball player who jumps for a rebound and unknowingly comes down on the top of another player's foot. Another basketball example is when a player runs to chase down a loose ball and when he attempts to stop too quickly while running at a high rate of speed, the momentum generated during the chase along with his entire body mass is still propelled forward. Stopping quickly and not having sufficient time to ensure proper placement of the foot or feet can cause severe stress on the athlete's ankle.

Under the aforementioned circumstances, the ankle is most vulnerable to injury (roll and sprain) because the athlete may want to stop, but the body weight and momentum and possibly the weight of another player or two, is disproportionately placed upon the ankle, causing it to turn or roll and therefore, become sprained.

The most common type of ankle sprain occurs when the foot is inverted, falling inward. When this type of ankle sprain happens, the outer or lateral ligaments are stretched too far. About 90% of ankle sprains are inversion injuries.[2] The other type of sprained ankle is called an eversion injury, where the foot is twisted outwards. When this occurs, the inner ligament is overstretched.

[2] http://orthopedics.about.com/cs/sprainsstranins/a/anklesprain.htm

Ankle sprains also occur during everyday activities. An unnatural twisting motion of the ankle joint can happen when the foot is planted awkwardly, when the ground or landing surface is uneven, or when an unusual amount of force is suddenly applied to the ankle joint. The issue of ankle sprains due to rolling of the foot to the outside edge while engaging in sporting activities is, by far, the most common injury for athletes and amateur sportsman alike.

Prior attempts to solve the problem of an ankle sprain due to rolling of the foot to the outside of the shoe sole, by redesigning the whole shoe support structure, or by immobilizing the side to the side movement of the entire ankle (similar to bracing in hockey skates) have met with only limited success.

U.S. Application No. 20110056097 (Ellis, III) discloses a shoe sole, including at least one insertable midsole orthotic. The insertable midsole orthotic is inserted within the shoe upper, the sides of which hold it in position. The shoe sole includes a concavely rounded side or underneath portion, which may be formed in part by the insertable midsole orthotic. U.S. Application No. 20110056093 (Ellis, III) discloses a shoe, including at least one removable midsole section formed by a midsole portion, wherein the removable midsole section is non-orthotic. The removable midsole section is inserted within the shoe upper, the sides of which hold it in position. The shoe sole includes a concavely rounded side or underneath portion, which may be formed in part by the removable midsole section.

U.S. Pat. No. 7,849,611 (Dean) discloses a built-in or added-on extension situated upon a side of a shoe (at the outer ankle) so as to minimize or prevent injury caused by inversion of a foot or ankle during athletic or other activities. The extension protrudes laterally out from the side of the shoe and generally spherically-shaped insert that may be constructed of a firm but slightly resilient material, such as a firm foam or firm rubber or neoprene.

U.S. Pat. No. 7,918,811 (Lussier; et al.) discloses support devices for joints of the human body. A support device for an ankle includes a main body having a medial portion and a lateral portion disposed about the ankle, and an interior surface; at least one of a medial support member disposed in a cavity in the medial portion of said main body and a lateral support member disposed in a cavity in the lateral portion of said main body; a strap disposed on a proximal portion of said main body.

U.S. Pat. No. 5,109,613 (Van Dyke) discloses a shoe with an integral ankle support preferably for an athletic shoe, having a plurality of adjustable straps and members attached to a shoe upper. The members provide semi-rigid support and are attached medially and laterally to the upper inner surface with a rivet in each member, thereby enabling movement of the members in an anterior and posterior direction about an axis defined by the rivets.

U.S. Pat. No. 4,366,634 (Giese; et al.) discloses an athletic shoe having an injection-molded intermediate portion bonding a fabric upper portion and a rubber outsole portion, for improved fit and comfort and decreased injury-causing fatigue, particularly adapted for use in the playing court-type sports such as basketball. The injection-molded intermediate portion conforms to and partially envelopes the metatarsal area and the heel area of the wearer's foot, and has an intermediate portion which gives lateral support to the instep area of a wearer's foot, such that the shoe moves as a unit together with the wearer's foot.

No prior attempts to embed a generally rigid brace structure external onto the shoe are known.

The primary object of the anti-roll ankle device of the present invention is to limit or prevent ankle sprains due to ankle rolling or turning, which frequently occurs during court-type sports, both amateur and professional or while jogging especially in real world situations (e.g., parks, sidewalks, wooded areas or streets). What is needed is an athletic shoe or device which will properly address the issue of ankle sprains due to rolling and turning and that provides the athlete with the confidence of full ankle support when it is most needed. What is needed is an athletic shoe or device with an additional support structure (be it to the inside and/or the outside edge of the rear sole of the shoe), or due to landing on an uneven surface, such as landing on another player's foot during a rebound; or by attempting a cross-over dribble and cutting too hard, without proper foot placement. Such unexpected and usually unavoidable injuries have severe consequences not to just the individual athlete, but also to the athlete's team, school, family and fans if said athlete is a key player for the team. If the athlete is an elite professional, an injured athlete can alter the outcome of playoff games, damage the brand or cause loss of revenue (both individually and to team or owner). Even if a player is able to play with an injured or sprained ankle, the player's level of play may be diminished.

SUMMARY OF THE INVENTION

The ankle inversion and eversion prevention shoe or device of the instant invention, addresses the aforementioned needs, and significantly limits or prevents ankle sprains due to rolling or turning that occur during aggressive athletic activity involving sports played on a court, such as basketball, volleyball, tennis, racquetball, squash, and handball and off court such as jogging and marathon activities.

A version of the athletic shoe of the instant invention comprises a cushioned padding or gel based inner plate or, and an elongated arm. The elongated arm is securely affixed to the inner plate or the shoe and both are sewn into the middle of the shoe, to the lower rear, partially enveloping the heel of the shoe. Located at the tip of the elongated arm, preferably under the tip, is a small piece of anti-grip rubber, permanently affixed to prevent the shoe from sliding or skidding while the athlete attempts to regain footing, with help from the durable brace. Alternatively, with the optional dual (or full) brace placed on the opposite side of the shoe, may provide comprehensive dual protection for inversion and eversion injuries alike. The athletic shoes that the present invention is specifically designed for concerns sports or activities relating to basketball, volleyball, tennis, racquetball, squash, and handball, but may be used in any athletic activity where high ankle sprains are a problem, including but not limited to jogging and marathon race activities.

A version of the ankle inversion and eversion prevention athletic shoe device of the present invention has an upper foot support portion and a shoe bottom. The athletic shoe is designed to prevent an athlete from spraining, rolling, or turning an ankle during an athletic activity. The brace is either located near the heel of the shoe, the middle of the shoe or abuts the side of the shoe in the general vicinity of the ankle. The brace preferably includes an elongated arm portion and a floor contact surface. The brace provides the athlete time to regain his or her balance onto the shoe bottom, thereby minimizing or preventing any ankle injury.

The ankle inversion and eversion prevention shoe device of the present invention comprises an athletic shoe having an affixed or insertable durable, lightweight brace. The brace is a reinforced durable airfoil-shaped wing-like structure embedded in an opening slot in the heel of the shoe. The athletic shoe preferably has a modified ankle inversion brace which is positioned at the rear of the foot, and lower portion of the shoe, wrapping partially around the heel at a specified angle or degree, with the heel being reinforced, so as to prevent collapse of the heel of the shoe during athletic play.

In one preferred embodiment of the ankle inversion and eversion prevention shoe of the present invention, a brace is inserted into an opening to the rear of the ankle of the athletic shoe and supporting the entire heel. The brace preferably wraps around the heel of the shoe protecting both types of ankle sprains. In another preferred embodiment of the ankle inversion and eversion prevention shoe device of the present invention, the shoe abuts one or both sides of the athlete's ankle.

In all embodiments, the brace extends a sufficient distance and at the appropriate angled degree above the bottom of said athletic shoe, so as not to interfere with ability of the athlete to compete aggressively and unimpeded by the shoe. The shoe brace is made of a material having sufficient strength as to be able to support the full weight of the athlete, should he or she land off-balance upon said shoe. The concept behind the device and placement of the brace on the shoe is to provide the athlete with time to regain his or her balance and get repositioned onto the shoe bottom, thereby minimizing or precluding any ankle injury.

For a complete understanding of the ankle inversion and eversion prevention shoe of the present invention, reference is made to the following detailed description and accompanying drawings in which the presently preferred embodiments of the athletic shoe of the invention are shown by way of example. As the invention may be embodied in many forms without departing from the spirit of essential characteristics thereof, it is expressly understood that the drawings are for purposes of illustration and description only, and are not intended as a definition of the limits of the invention.

DETAILED DESCRIPTION OF THE PREFERRED EMBODIMENTS

Figure 1A:
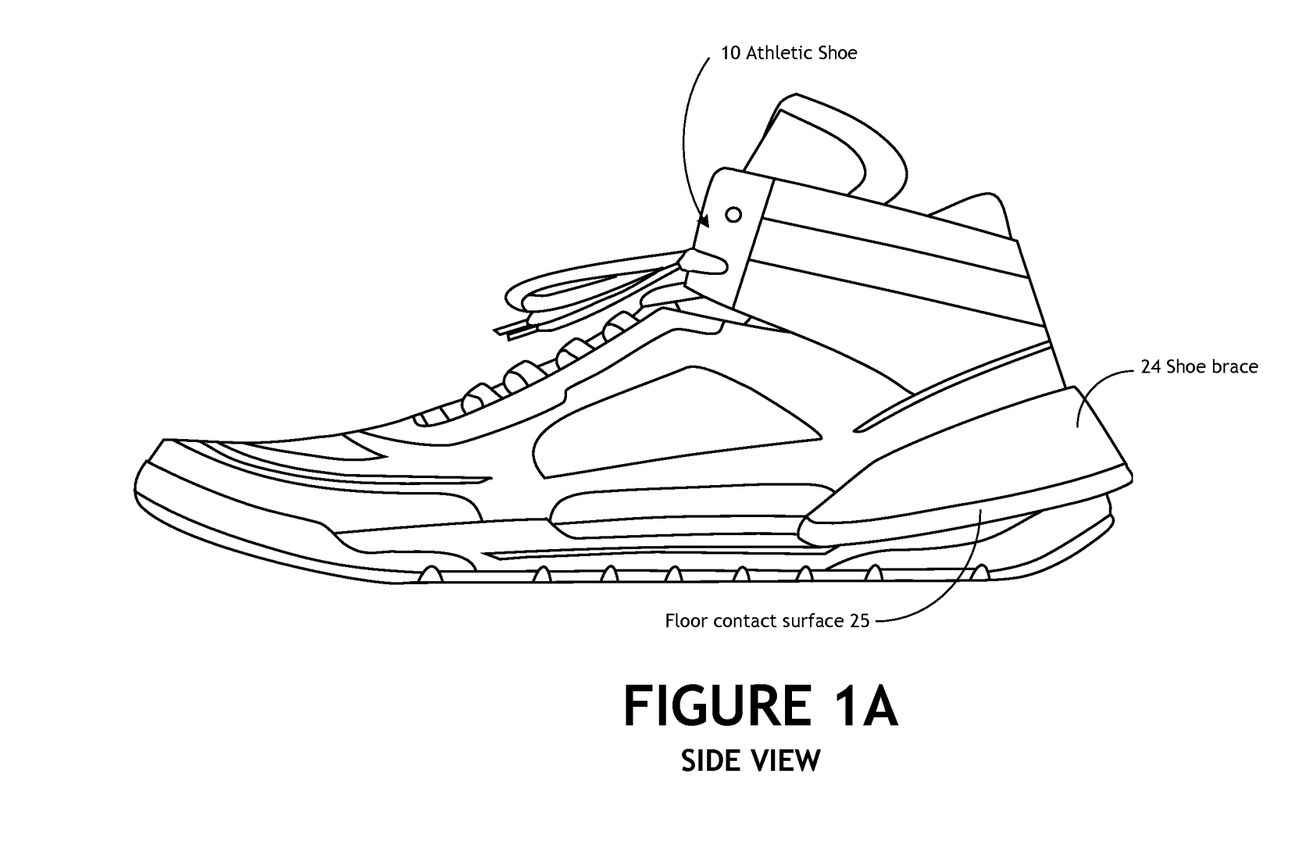
FIG. 1A depicts a side perspective view of a first preferred embodiment of the ankle inversion and eversion prevention shoe device of the present invention with the brace attached to the heel portion of the ankle inversion and eversion prevention shoe device and abutting the ankle. The design also depicts the attachment point and the polymer or anti-grip, rubber-floor contact surface.

Referring now to the drawings, FIG. 1A depicts the side view of the 1$^{st}$ preferred embodiment of the athletic shoe [10] of the present invention, with a modified ankle inversion and eversion device [40] which is attached rearward and downward toward the heel on the athletic shoe [10]. The heel of the shoe [10] is reinforced with a hard, break resistant material, such as carbon fiber, polyurethane, or hard plastic. The modified ankle inversion and eversion device [40], also has an anti-slip floor contact point [25] which may be made from any friction providing material, such as hard rubber, polyurethane, or other material. This tip is preferably permanently affixed, or in some instances is replaceable.

Figure 1B:
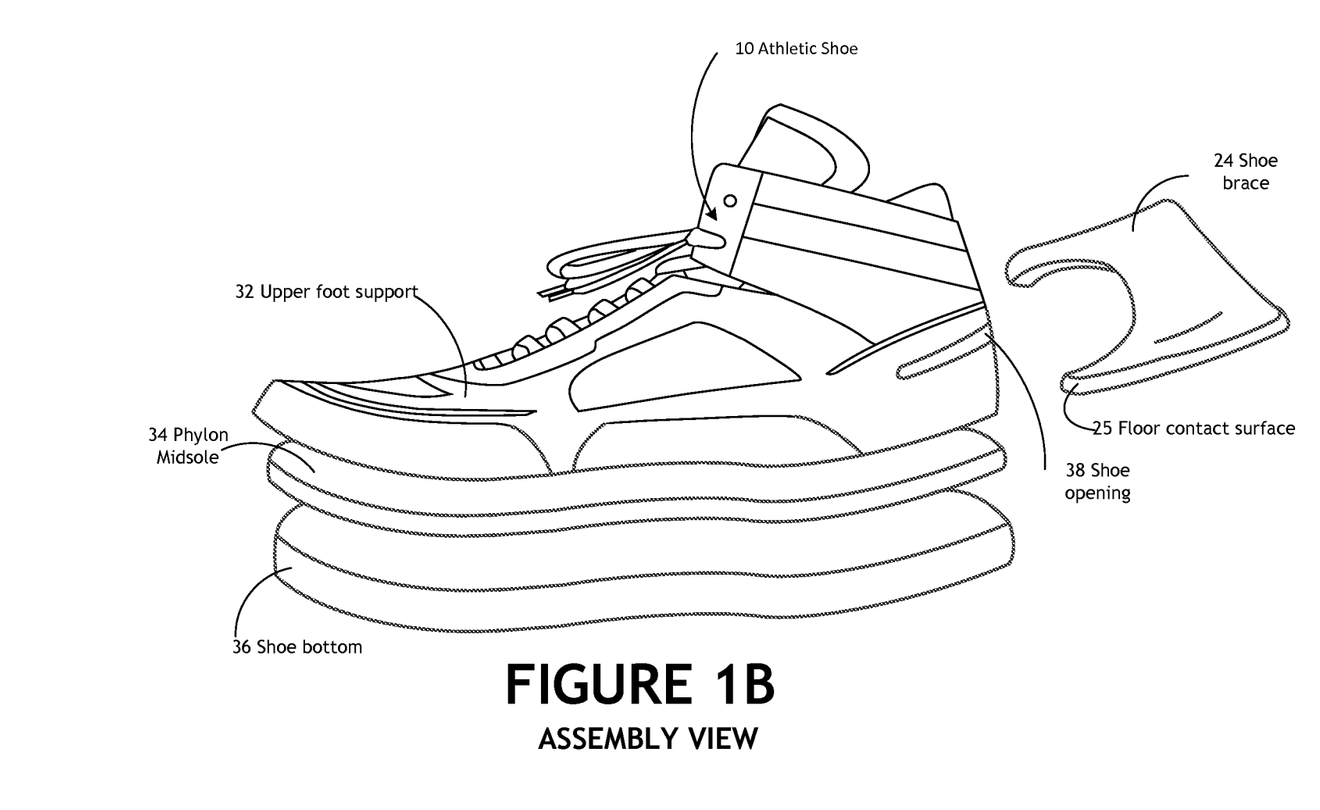
FIG. 1B depicts an assembly view of the first preferred embodiment of the ankle inversion and eversion prevention shoe device of the present invention with the anti-ankle inversion/eversion device of FIG. 1A.

FIG. 1B depicts an assembly view of the first preferred embodiment of the ankle inversion and eversion prevention shoe device of the present invention with anti-ankle inversion and eversion device of FIG. 1A. The assembly depicts the upper foot support, the phylite® midsole (phylite is a registered trademark of the Nike Corp.), the shoe bottom, and the shoe being insertable in a narrow opening near the heel of the upper foot support.

Figure 2:
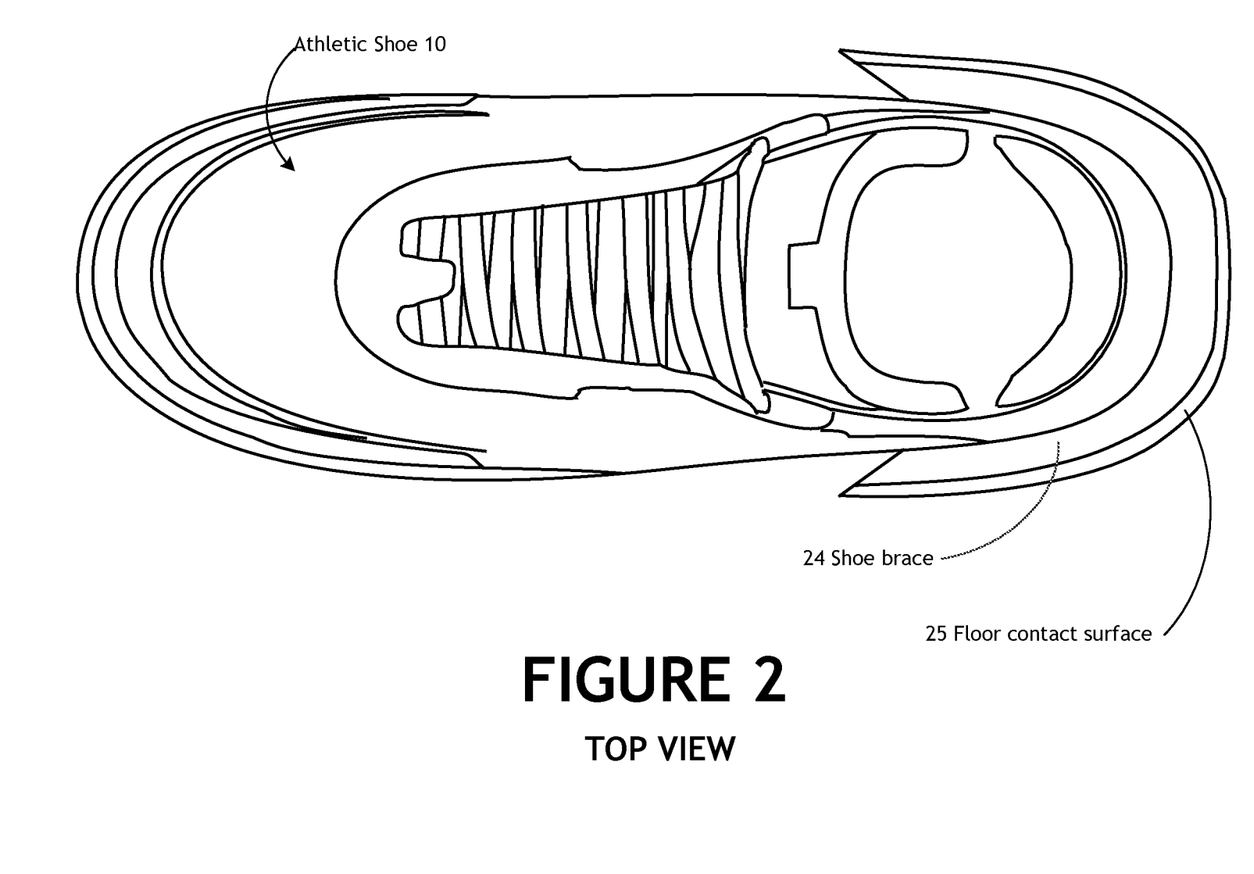
FIG. 2 depicts a top perspective view of the first preferred embodiment of the ankle inversion prevention shoe with the ankle inversion and eversion device of FIGS. 1A and 1B.

FIG. 2 depicts the top view of the first preferred embodiment of the ankle inversion and eversion prevention shoe device [10] of the present invention, with the ankle inversion and eversion device [140] wrapping completely around the heel of the athletic shoe.

Figure 3:
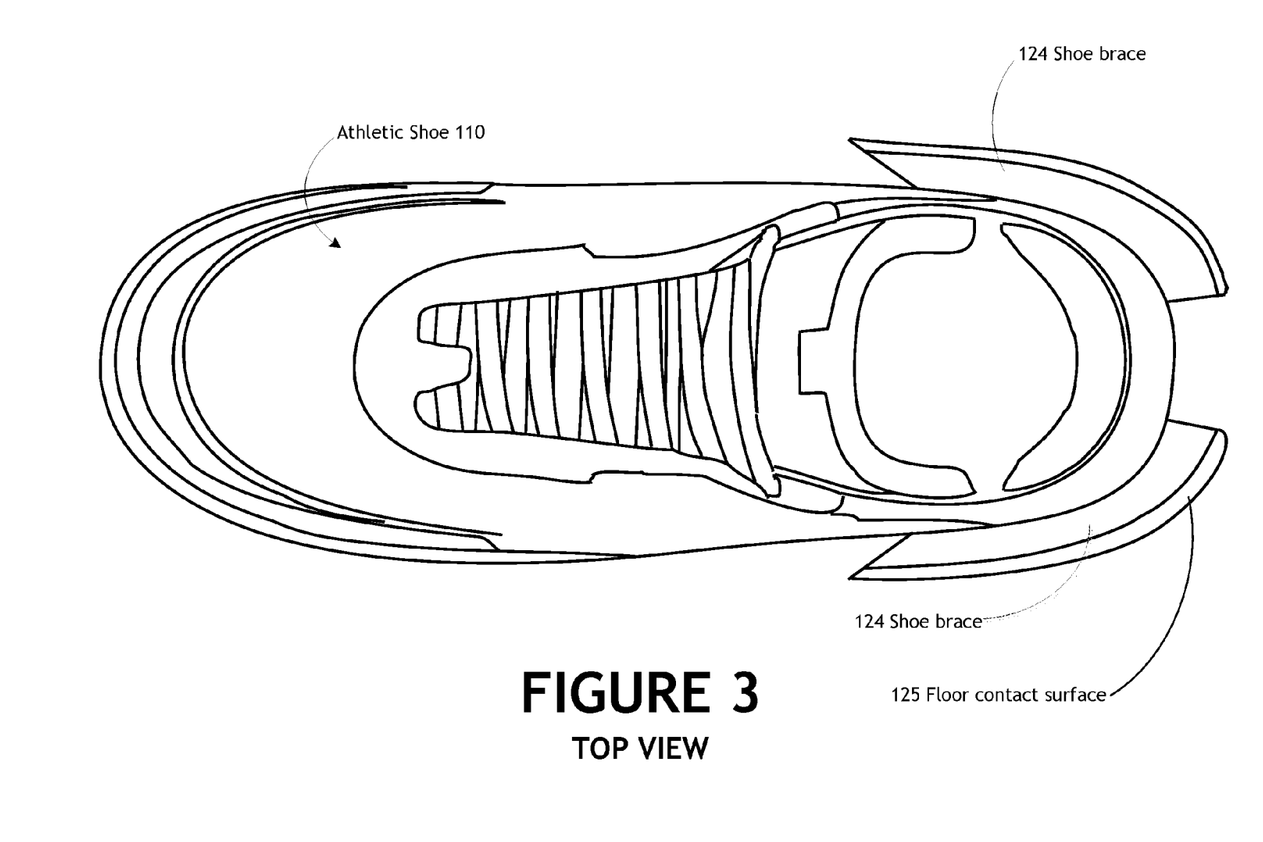
FIG. 3 depicts a top perspective view of a second preferred embodiment of the ankle inversion and eversion prevention shoe with the ankle inversion device of FIG. 1A.

FIG. 3 depicts the top view of the second preferred embodiment of the ankle inversion and eversion prevention shoe [110] of the present invention, with the modified ankle inversion device [40]. In addition, the ankle inversion and eversion device (140) is inserted or permanently affixed into either one or two slots (not shown) near the heel of the shoe, mirroring the location depicted in FIG. 1B.

Figure 4:
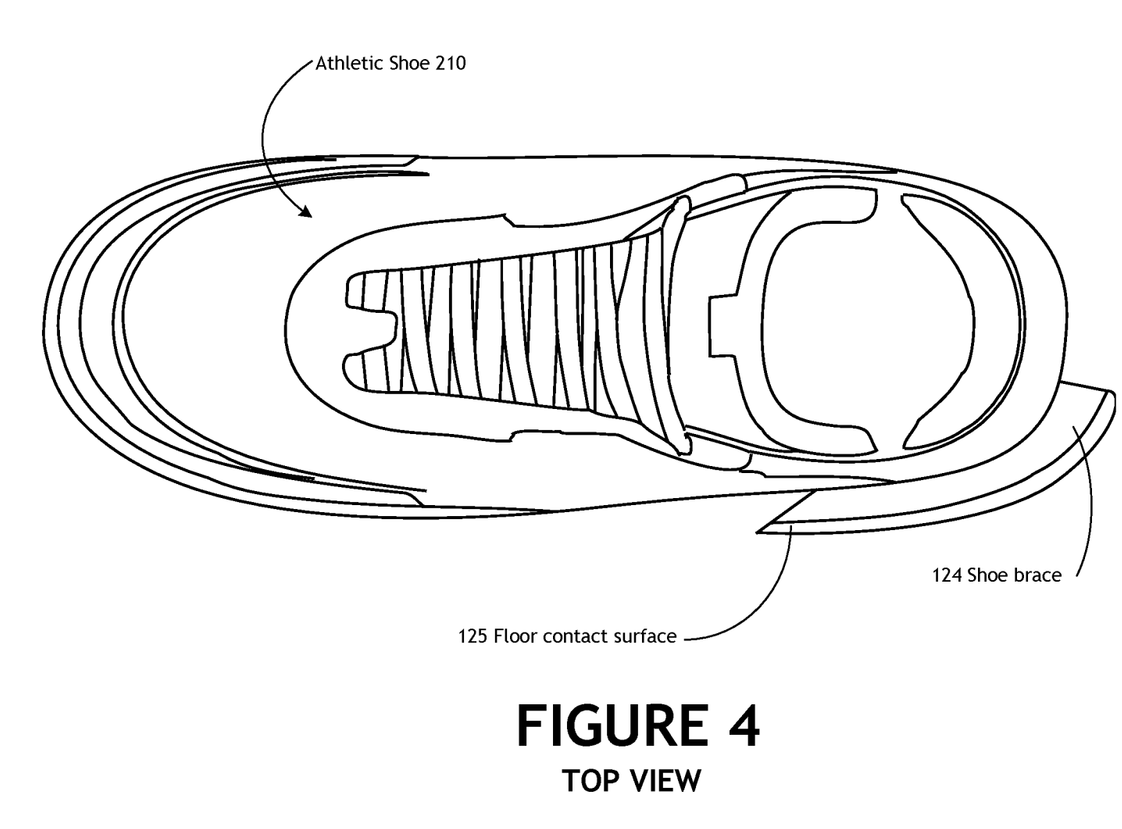
FIG. 4 depicts a top perspective view of a third preferred embodiment of the ankle inversion and eversion prevention shoe with the ankle inversion and eversion device of FIG. 1A.

FIG. 4 depicts the top view of the third preferred embodiment of the ankle inversion prevention shoe [210] of FIG. 1A, with the modified ankle inversion device [140] being shown from the top attached to the outside edge of the shoe [210]. In this depiction, the modified inversion device [40], wraps partially around the heel.

Figure 5:
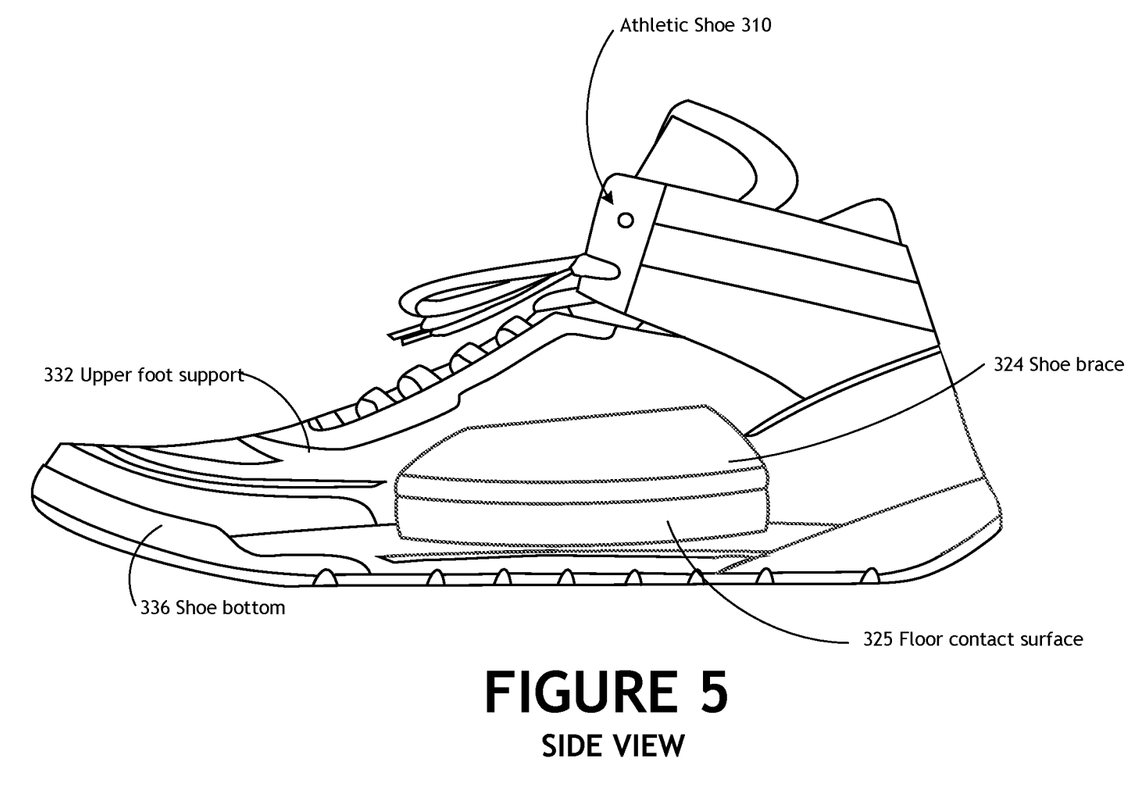
FIG. 5 depicts a side perspective view of a fourth preferred embodiment of the ankle inversion and eversion prevention shoe device of the present invention with the brace attached to the side of the ankle inversion and eversion prevention shoe positioned on the side of the shoe in the general vicinity of the ankle.

FIG. 5 depicts a side perspective view of a fourth preferred embodiment of the ankle inversion and eversion prevention shoe [310] of the present invention with the anti-ankle inversion and eversion device of the present invention [324] attached to the side of the ankle inversion and eversion prevention shoe [310] being disposed on the side of the shoe, and preferably abutting or being slightly forward of the ankle, with a gel insert sewn into the heel for additional comfort for the wearer. The device [324] extends at least 1" from the bottom of the shoe and is built to withstand at least 350 pounds of pressure. The athletic shoe [310] protects the athlete against both inverted and eversion type ankle injuries. This shoe [310] preferably protrudes about three-and-one-half inches from the ankle sloped downwardly, in a concave manner.

The shoe brace [324] extends a sufficient distance above the bottom of said athletic shoe [310] so as not to interfere with ability of the athlete to compete aggressively and unimpeded by the shoe. The shoe brace [324] is preferably made of a material having sufficient strength as to be able to support the full weight of the athlete should he or she land off-balance upon said shoe brace [324].

Figure 6:
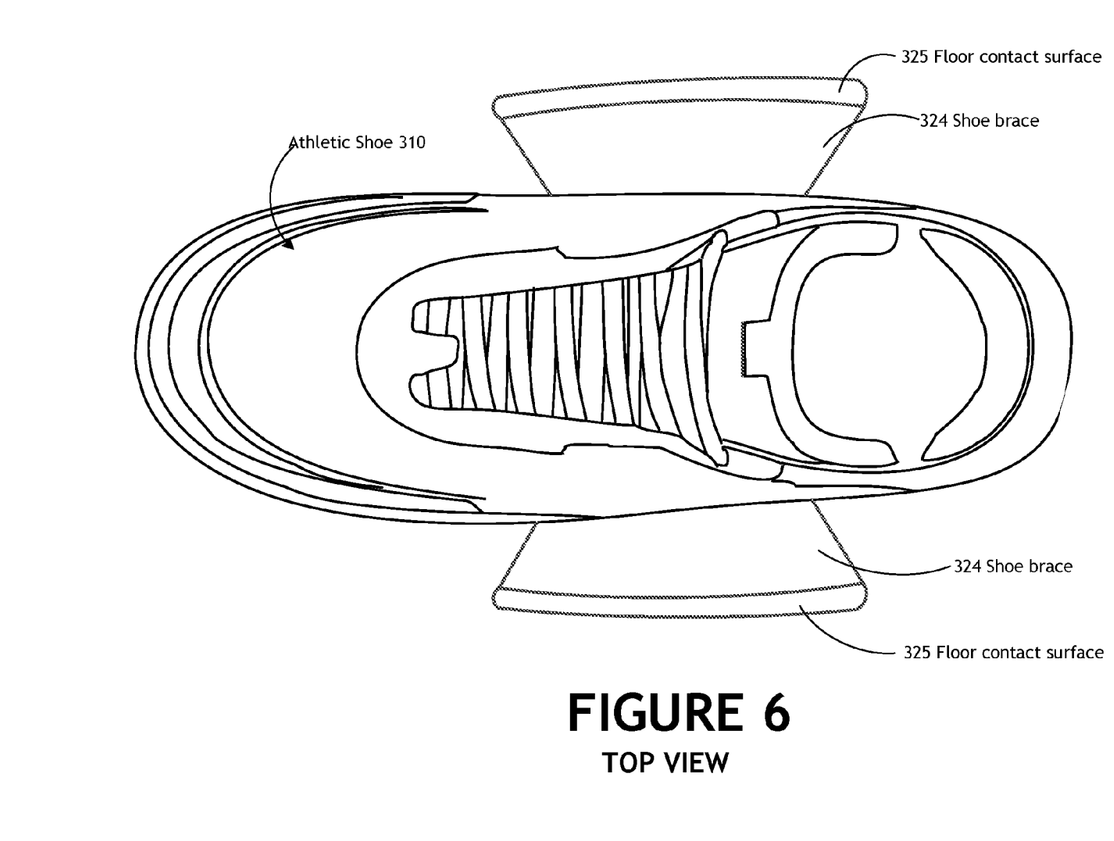
FIG. 6 depicts a top perspective view of the fourth preferred embodiment of the ankle inversion and eversion prevention shoe device with the ankle inversion and eversion device of FIG. 5.

FIG. 6 depicts a top perspective view of the fourth preferred embodiment of the ankle inversion and eversion prevention shoe [310] with the ankle inversion and eversion device [324] of FIG. 5. FIG. 3 depicts a front perspective view of a fourth preferred embodiment of the athletic shoe [310] of the present invention with an inside and outside angle stabilization brace [310] attached to the shoe stabilizing both sides of the ankle. The inside and outside angle stabilization braces [324] are affixed to the shoe attachment [322]. The hardened polymer or anti-slip rubber floor contact surface [325] is secured to each shoe [324].

Figure 7:
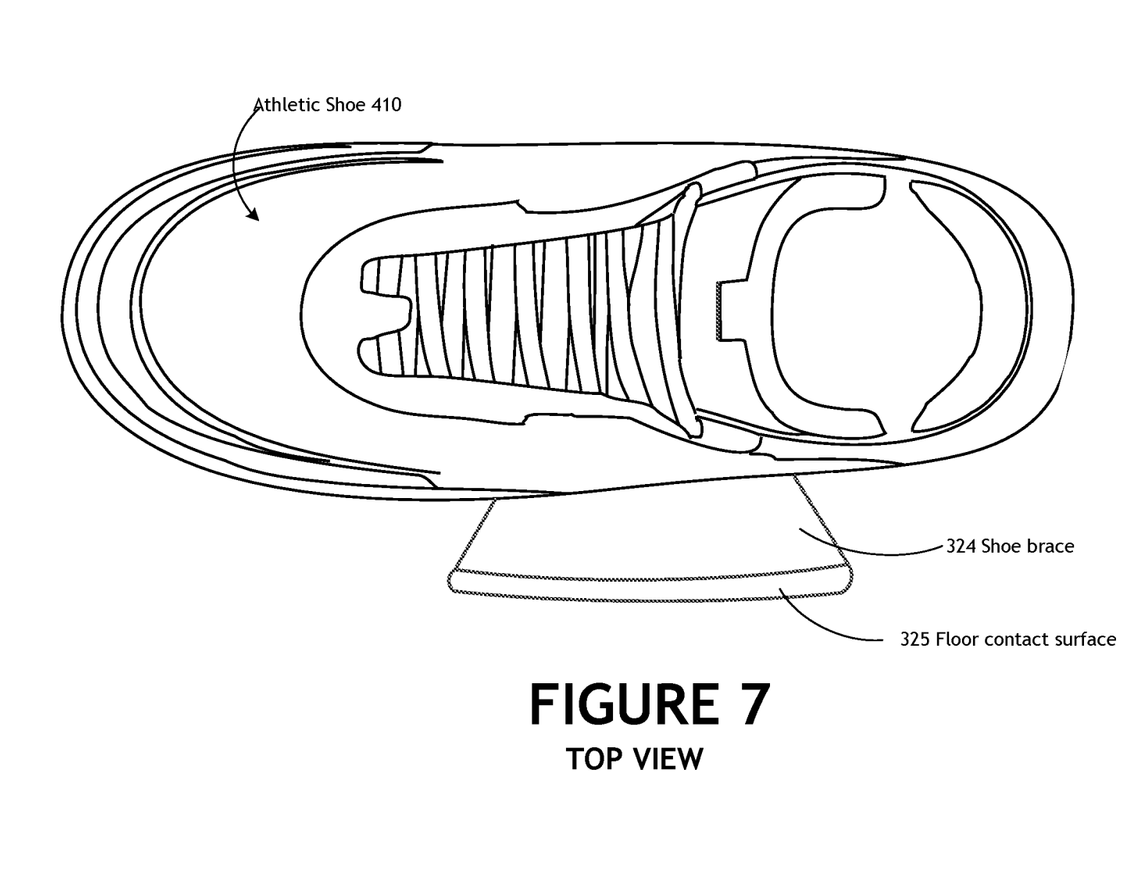
FIG. 7 depicts a top perspective view of the fifth preferred embodiment of the ankle inversion and eversion prevention shoe with the ankle inversion and eversion device of FIG. 5.

FIG. 7 depicts a top perspective view of the fifth preferred embodiment of the ankle inversion prevention shoe [410] with the ankle inversion device of FIG. 5. Only one side of the ankle is supported in this embodiment to preclude inversion.

Figure 8:
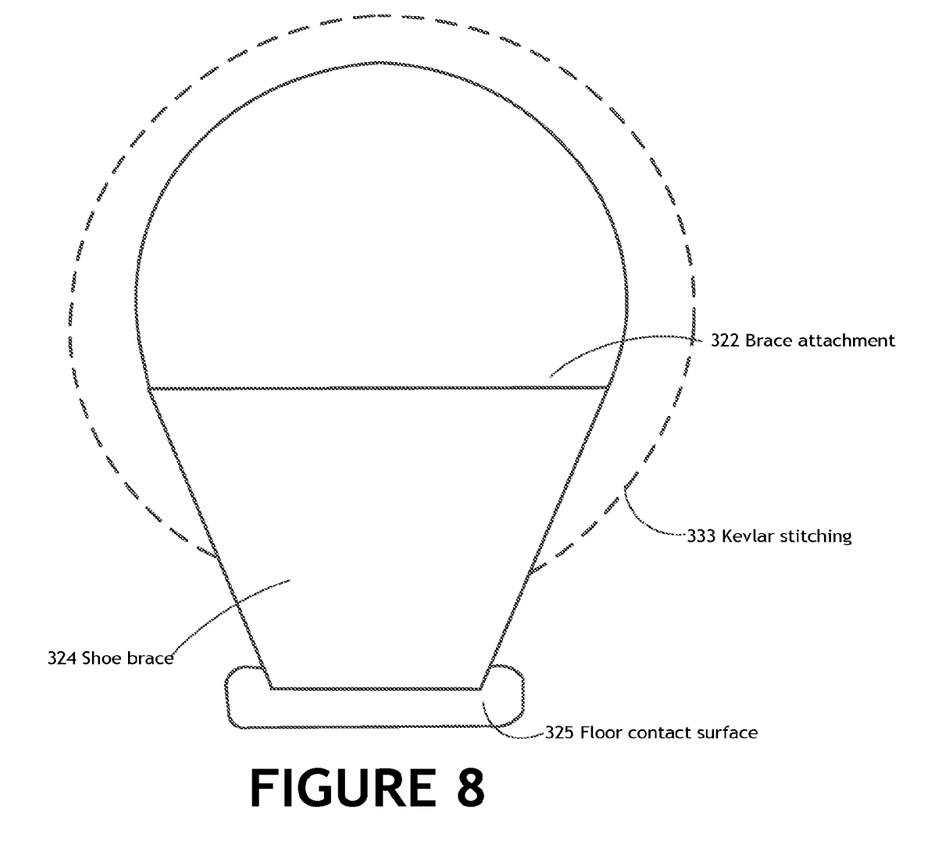
FIG. 8 depicts the angle stabilization shoe of the ankle inversion and eversion prevention shoe device of FIG. 5, with the attachment point and the polymer or anti-grip, rubber-floor contact surface.

FIG. 8 depicts the angle stabilization shoe of the ankle inversion/eversion prevention shoe of FIG. 5, with the attachment point and the polymer or anti-grip, rubber-floor contact surface. The shoe brace [324] and the shoe attachment [322] are detailed in FIG. 8. The shoe attachment [322] preferably comprises a piece of high strength durable plastic, polymer, rubber, or carbon fiber and is attached directly to the shoe during manufacture and is affixed at the middle of the shoe. Behind the shoe attachment [322] is a layer of foam or gel which is used to provide greater comfort to the wearer of the shoe when weight is disproportionately placed on the inner or outer ankle and significantly limits or eliminates the angle roll or turning during athletic activity. The shoe attachment [322] is affixed and manufactured into the shoe during production, preferably with Kevlar® stitching [333].

Figure 9A:
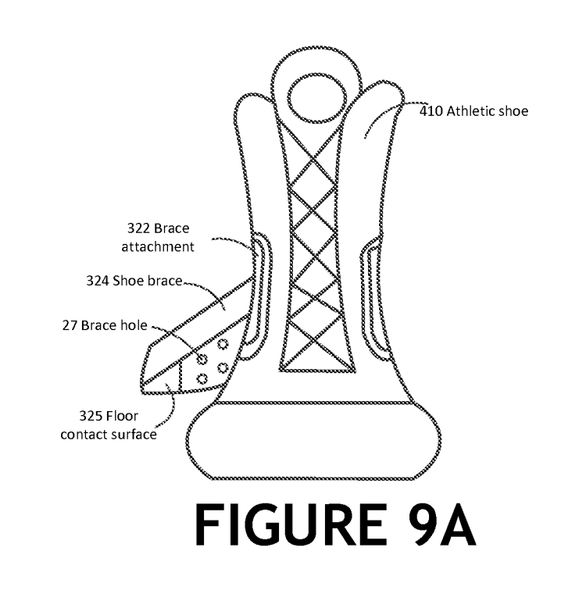
FIG. 9A depicts a front perspective view of yet another preferred embodiment of the ankle inversion and eversion prevention shoe device of the present invention with the anti-ankle inversion and eversion device of FIG. 6, with an outside and inside brace attached at the outer of the shoe placed near the middle of the foot or towards the rear of the heel.

FIG. 9A depicts a front perspective view of yet another preferred embodiment of the athletic shoe [410] of the present invention, with another shoe [324] similar to the anti-ankle inversion device of FIG. 5 and shoe design [24] attached to the outside portion at the inner of the shoe [410] at the ankle. The shoe [24] shall have several air passages drilled in the side-placed shoe to enable air to pass freely through while the athlete is running, and preclude the athlete from being slowed during play, while maintaining the requisite durability.

Figure 9B:
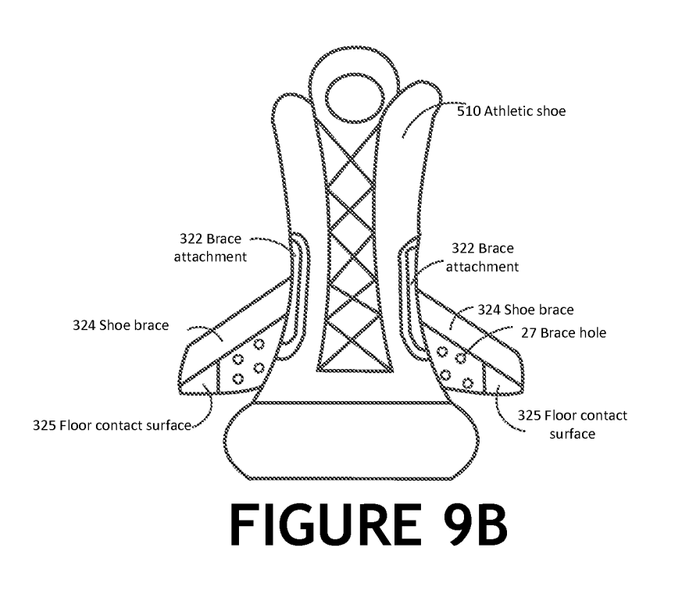
FIG. 9B depicts a front perspective view of still yet another preferred embodiment of the ankle inversion and eversion prevention shoe of the present invention with the anti-ankle inversion and eversion device of FIG. 6, with both an outside and inside brace attached at the outer and inner of the shoe, placed near the middle of the foot or towards the rear of the heel.

FIG. 9B depicts a front perspective view of still yet another preferred embodiment of the athletic shoe [510] of the present invention, with the anti-ankle inversion and eversion device of FIG. 5 attached both on the outside and inside of the shoe [510] at the ankle, respectively. The shoe [24] preferably have several holes [27] drilled into the side-placed shoe enabling air to pass through, and preclude the athlete from being slowed during play.

The shoe assembly itself is a carbon fiber or other lightweight unbreakable polymer and is attached to a plate of similar composition with soft foam or gel backing affixed to the side of the plate of the shoe. Inside the shoe, there is a gel or soft foam padded cushion also affixed to the position where the shoe is attached. This increases user comfort in the circumstance when the athlete's weight is rolled disproportionately toward the inner or outer ankle. Located at the tip of the shoe and angled down toward the surface floor, is a polymer or anti-grip rubber tip, designed to enable the athlete's foot to move with the floor and not grip the surface while at the same time, giving the athlete time to regain footing, possible by the shoe preventing the roll.

Figure 10A:
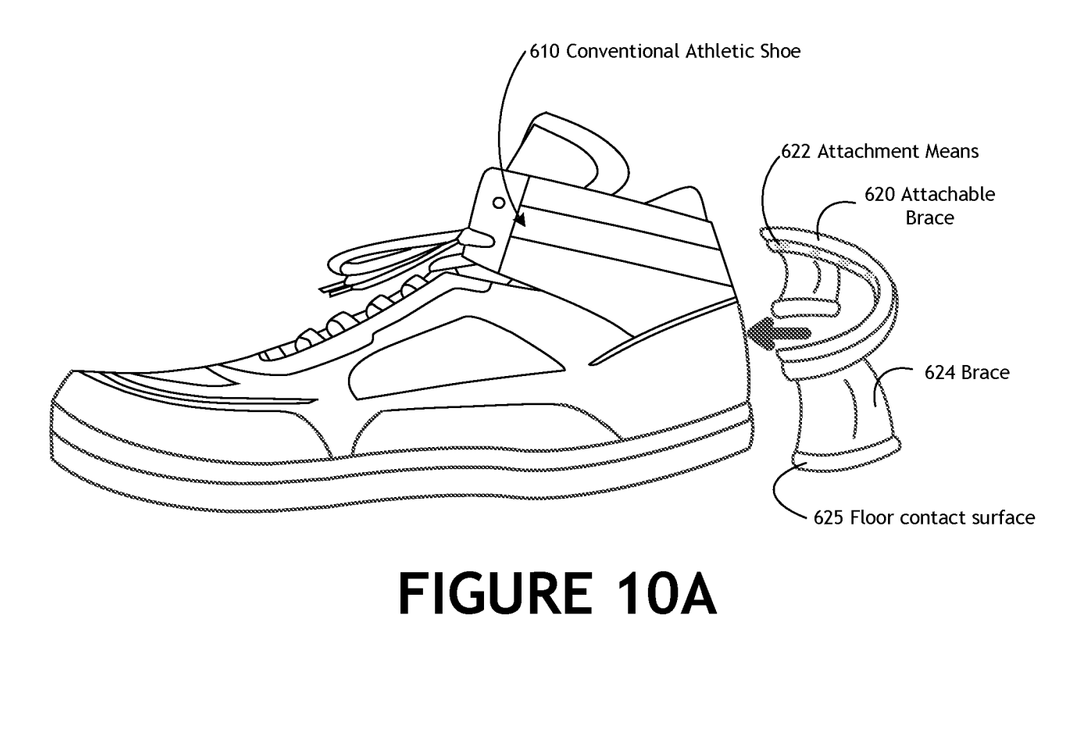
FIG. 10A depicts a side perspective view of a first preferred embodiment of the ankle inversion and eversion prevention shoe brace of the present invention with the brace being attachable to the heel of a conventional shoe, said shoe brace being made of a rigid plastic material that snap fits on the conventional shoe, said shoe brace being attachable to said shoe by conventional means.

FIG. 10A depicts a side perspective view of a first preferred embodiment of the ankle inversion and eversion prevention shoe brace of the present invention [624] with the brace being attachable to the heel of a conventional shoe [610]. The shoe brace [624] is made of a rigid but durable plastic material that snap fits onto the heel of a conventional shoe [610]. The shoe brace is attachable to the shoe [610] by conventional means. The brace [624] is securely attached to the shoe [610] so that it will not slip, by conventional means [622], such as by gluing compounds, adhesive compounds, straps, laces, hook and loop fasteners (such as Velcro®), or a combination of these. The ankle inversion and eversion prevention shoe brace of the present invention [624] is also attachable directly to the foot of a person over a sweat sock with chronically weak ankles or healing from an ankle injury (not shown). When the brace [624] is securely attached directly to the foot over a sweat sock, the attachment means are preferably straps, laces, hook and loop fasteners (such as Velcro®), or a combination of these.

Figure 10B:
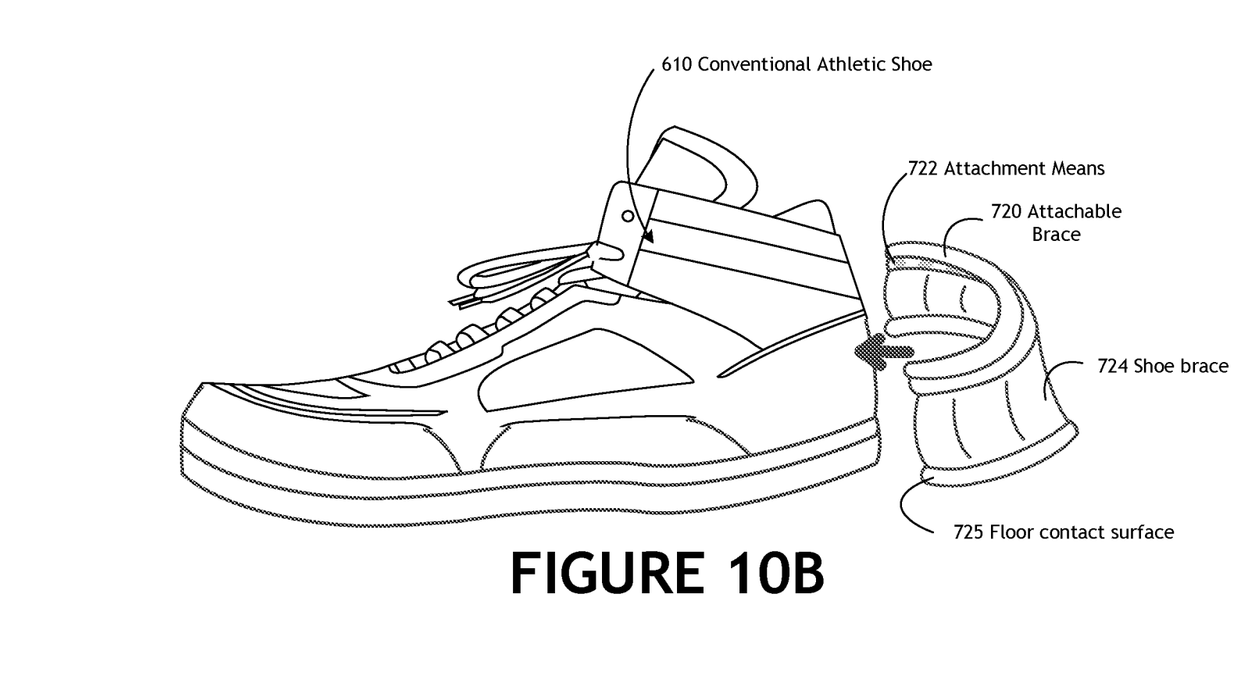
FIG. 10B depicts a side perspective view of a second preferred embodiment of the ankle inversion and eversion prevention shoe brace of the present invention with the brace being attachable to the heel of a conventional shoe, said shoe brace being made of a rigid plastic material that snap fits on the conventional shoe, said shoe brace being attachable to said shoe by conventional means.

FIG. 10B depicts a side perspective view of a second preferred embodiment of the ankle inversion and eversion prevention shoe brace of the present invention [724] with the brace being attachable to the heel of a conventional shoe [624]. The shoe brace [724] is made of a rigid but durable plastic material that snap fits onto the heel of a conventional shoe [610]. The brace [724] is securely attached to the shoe [610] so that it will not slip, by conventional means [722], such as by gluing compounds, adhesive compounds, straps, laces, hook and loop fasteners (such as Velcro®), or a combination of these. The ankle inversion and eversion prevention shoe brace of the present invention [724] is also attachable directly to the foot of a person over a sweat sock with chronically weak ankles or healing from an ankle injury (not shown). When the brace [724] is securely attached directly to the foot over a sweat sock, the attachment means are preferably straps, laces, hook and loop fasteners (such as Velcro®), or a combination of these.

Throughout this specification, there are various Patents/Applications referenced by application number and inventor. The disclosures of these Patents/Applications are hereby incorporated by reference in their entireties into this specification in order to more fully describe the state-of-the-art.

It is evident that many alternatives, modifications, and variations of the ankle inversion prevention shoe of the present invention are disclosed herein will be apparent to those skilled in the art in light of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

Parts List

10. Athletic shoe device ($1^{st}$ embodiment)
24. Shoe brace
25. Floor contact surface
27. Brace holes
32. Upper foot support
34. Phylon Midsole
36. Shoe Bottom
38. Shoe opening
110. Athletic shoe ($2^{nd}$ embodiment)
124. Shoe Brace
125. Floor contact surface
210. Athletic shoe ($3^{rd}$ embodiment)
310. Athletic shoe ($4^{th}$ embodiment)
322. Attachment
324. Shoe Brace
325. Floor contact surface
332. Upper foot support
333. Kevlar Attachment
336. Shoe Bottom
410. Athletic shoe ($5^{th}$ embodiment)
510. Athletic shoe ($6^{th}$ embodiment)
610. Conventional Athletic Shoe
624. Shoe Brace
625. Floor contact surface
620. Attachable Brace ($1^{st}$ embodiment)
622. Adhesive Means
720. Attachable Brace ($2^{nd}$ embodiment)
722. Adhesive Means
724. Shoe Brace
725. Floor contact surface

I claim:

1. An athletic shoe to be worn on a foot of an athlete during an athletic activity, the athletic shoe comprising:
    a shoe bottom defining a sole of the athletic shoe having a bottom surface for contacting the ground;
    an upper foot support secured to the shoe bottom and extending above the shoe bottom;
    a shoe brace connected to the athletic shoe along a heel region, a top portion of shoe brace contacting the upper foot support and an angled portion of the shoe brace extending away from the athletic shoe so that a lower surface of the shoe brace is positioned external to the athletic shoe such that the lower surface is spaced apart from the shoe bottom and positioned a distance above the ground when the bottom surface of the athletic shoe contacts the ground evenly; and an anti-slip material positioned along the lower surface of the shoe brace, the anti-slip material preventing the shoe brace from sliding or skidding while the athlete is regaining his or her balance, wherein the shoe brace is essentially rigid to provide lateral support to the athlete when the bottom surface of the shoe bottom contacts the ground unevenly such that the lower surface of the shoe brace contacts the ground, the shoe brace thereby providing the athlete time to regain his or her balance, thereby minimizing any ankle spraining, rolling, or turning.

2. The athletic shoe of claim 1, wherein the lower surface of the shoe brace is spaced apart from the shoe bottom by a distance being less than one inch so as not to interfere with ability of the athlete to compete aggressively and be unimpeded by the shoe brace.

3. The athletic shoe of claim 1, wherein the shoe brace has a longitudinal curvature such that the top surface of the shoe brace is generally parallel to the heel region, wherein the curvature extends from a first lateral side of the athletic shoe and curves around to a rear side of the athletic shoe along the heel region.

4. The athletic shoe of claim 3, wherein the brace extends from the first lateral side to a second lateral side so that the curvature extends around the entire rear side of the athletic shoe.

5. The athletic shoe of claim 1, wherein the shoe brace is formed of a material including at least one of metal, plastic, polymer, rubber, and carbon fiber.

6. The athletic shoe of claim 1, further comprising two shoe braces, a first shoe brace positioned to provide lateral support in a first lateral direction to an ankle of the athlete to prevent ankle inversion, a second shoe brace positioned to provide lateral support in a second lateral direction to the ankle of the athlete to prevent ankle eversion.

7. Athletic footwear to be worn on a foot of an athlete during an athletic activity, the athletic footwear comprising:
a footwear bottom defining a sole of the footwear having a bottom surface for contacting the ground;
an upper foot support secured to the shoe bottom and extending above the footwear bottom;
a brace attached above the shoe bottom along a lateral side of the athletic footwear, a top portion of the brace abutting the upper foot support and an angled portion of the brace extending away from the athletic footwear so that a lower surface of the brace is positioned external to the athletic shoe such that the lower surface is spaced apart from the footwear bottom and positioned a distance above the ground when the bottom surface of the footwear contacts the ground evenly; and
anti-slip material positioned at an end of the brace, the anti-slip material preventing the brace from sliding or skidding,
wherein the lower surface of the brace contacts the ground when the bottom surface of the footwear bottom contacts the ground unevenly, the brace thereby providing lateral support by transferring force from the ground to the upper foot support for minimizing ankle inversion and eversion.

8. The athletic footwear of claim 7, further comprising two braces, a first brace positioned to provide lateral support for in a first lateral direction to an ankle of the athlete from ankle inversion, a second brace positioned to provide lateral support in a second lateral direction of the ankle of the athlete from ankle eversion.

9. The athletic footwear of claim 7, wherein the brace has a curvature such that the top portion of the brace is generally parallel to a heel portion of the footwear so that the brace extends from the lateral side of the footwear and curves around to at least a portion of a rear side of the footwear.

10. The athletic footwear of claim 9, wherein the brace extends from the lateral side to a second lateral side so that the curvature extends around the entire rear side of the footwear.

11. The athletic footwear of claim 7, wherein the brace is formed of a material including at least one of metal, plastic, polymer, rubber, and carbon fiber.

12. The athletic footwear of claim 7, wherein the brace is generally rigid and supports up to three hundred pounds of force when in contact with the ground.

13. An athletic shoe to be worn on a foot of an athlete during an athletic activity, the athletic shoe comprising:
a shoe bottom defining a sole of the athletic shoe having a bottom surface for contacting the ground;
an upper foot support secured to the shoe bottom and extending above the shoe bottom;
a first shoe brace connected to the athletic shoe along a first lateral side at a heel region of the shoe, the first shoe brace having a first top portion that abuts the upper foot support and a first angled portion extending away from the athletic shoe so that a first lower surface is spaced apart from the shoe bottom,
a second shoe brace connected to the athletic shoe along a second lateral side at the heel region of the shoe, the second shoe brace having a second top portion that abuts the upper foot support and a second angled portion extending away from the athletic shoe so that a second lower surface of the second brace is spaced apart from the shoe bottom; and
an anti-slip material positioned along each of the first and second lower surfaces of the shoe brace, the anti-slip material preventing the shoe brace from sliding or skidding while the bottom surface of the shoe contacts the ground unevenly,
wherein when the bottom surface of the athletic shoe contacts the ground evenly, the first and second lower surfaces are positioned at a distance above the ground,
wherein when a first side of the bottom surface of the athletic shoe contacts the ground unevenly, the first lower surface of the first shoe brace contacts the ground and provides lateral support in a first lateral direction to an ankle of the athlete to prevent ankle inversion, and
wherein when a second side of the bottom surface of the athletic shoe contacts the ground unevenly, the second lower surface of the shoe brace contacts the ground and provides lateral support in a second lateral direction to the ankle of the athlete to prevent ankle eversion.

14. The athletic shoe of claim 13, wherein the first and second lower surfaces of the shoe brace are both spaced apart from the shoe bottom by a distance being less than one inch so as not to interfere with ability of the athlete to compete aggressively and be unimpeded by the shoe brace.

15. The athletic shoe of claim 13, wherein the first and second shoe braces have a longitudinal curvature such that the first and second top portions of the shoe braces are generally parallel to the heel region, wherein the curvature extends from a side of the athletic shoe and curves around to a rear side of the athletic shoe.

16. The athletic shoe of claim 13, wherein the first and second shoe braces are formed of a material including at least one of metal, plastic, polymer, rubber, and carbon fiber.

17. The athletic shoe of claim 13, wherein the first and second braces are generally rigid and each support up to three hundred pounds of force when in contact with the ground.

* * * * *